United States Patent
Moine et al.

(10) Patent No.: US 10,758,640 B2
(45) Date of Patent: Sep. 1, 2020

(54) SKIN-ADHESIVE SILICONE GEL

(71) Applicant: ELKEM SILICONES FRANCE SAS, Lyons (FR)

(72) Inventors: Caroline Moine, Sorbiers (FR); Maryline Quemin, Villeurbanne (FR); Gaelle Cros, Ternay (FR)

(73) Assignee: ELKEM SILICONES FRANCE SAS, Lyons (FR)

( * ) Notice: Subject to any disclaimer, the term of this patent is extended or adjusted under 35 U.S.C. 154(b) by 0 days.

(21) Appl. No.: 16/086,000

(22) PCT Filed: Mar. 16, 2017

(86) PCT No.: PCT/FR2017/000051
§ 371 (c)(1),
(2) Date: Sep. 17, 2018

(87) PCT Pub. No.: WO2017/158250
PCT Pub. Date: Sep. 21, 2017

(65) Prior Publication Data
US 2019/0099517 A1    Apr. 4, 2019

(30) Foreign Application Priority Data
Mar. 17, 2016  (FR) .................................... 16 00444

(51) Int. Cl.
| *G05B 19/10* | (2006.01) |
| *H01R 43/048* | (2006.01) |
| *A61L 27/18* | (2006.01) |
| *C09J 183/04* | (2006.01) |
| *C08L 83/04* | (2006.01) |
| *C08K 5/56* | (2006.01) |
| *C08L 83/00* | (2006.01) |
| *A61L 24/04* | (2006.01) |
| *A61L 15/58* | (2006.01) |
| *A61L 15/26* | (2006.01) |
| *A61L 26/00* | (2006.01) |
| *A61L 27/34* | (2006.01) |
| *C08G 77/12* | (2006.01) |
| *C08G 77/20* | (2006.01) |
| *C08L 75/04* | (2006.01) |

(52) U.S. Cl.
CPC .............. *A61L 27/18* (2013.01); *A61L 15/26* (2013.01); *A61L 15/585* (2013.01); *A61L 24/043* (2013.01); *A61L 26/0019* (2013.01); *A61L 27/34* (2013.01); *C08K 5/56* (2013.01); *C08L 83/00* (2013.01); *C08L 83/04* (2013.01); *C09J 183/04* (2013.01); *C08G 77/12* (2013.01); *C08G 77/20* (2013.01); *C08L 75/04* (2013.01); *C08L 2203/02* (2013.01); *C08L 2205/025* (2013.01); *C08L 2205/03* (2013.01); *C08L 2312/00* (2013.01)

(58) Field of Classification Search
None
See application file for complete search history.

(56) References Cited

U.S. PATENT DOCUMENTS

| 3,159,601 A | 12/1964 | Ashby |
| 3,159,602 A | 12/1964 | Hamilton et al. |
| 3,220,972 A | 11/1965 | Lamoreaux |
| 3,419,593 A | 12/1968 | Willing |
| 3,508,947 A | 4/1970 | Hughes |
| 3,632,374 A | 1/1972 | Greiller et al. |
| 3,775,452 A | 11/1973 | Karstedt |
| 4,479,987 A | 10/1984 | Koepke et al. |
| 4,830,887 A | 5/1989 | Reiter |
| 4,933,215 A | 6/1990 | Naruse et al. |
| 4,974,533 A | 12/1990 | Ishizuka et al. |
| 8,586,191 B2 | 11/2013 | Lorentz et al. |

FOREIGN PATENT DOCUMENTS

| EP | 0057459 | 8/1982 |
| EP | 0188978 | 7/1986 |
| EP | 0190530 | 8/1986 |
| EP | 0322118 | 6/1989 |
| EP | 0537086 | 4/1993 |
| WO | 2005/051442 | 6/2005 |
| WO | 2008/057155 | 5/2008 |
| WO | 2011/092404 | 8/2011 |
| WO | 2014/131999 | 9/2014 |

OTHER PUBLICATIONS

International Search Report and Written Opinion dated Sep. 21, 2017 in corresponding International Patent Application No. PCT/FR2017/000051, filed Mar. 16, 2017, 11 pages.

*Primary Examiner* — Jeffrey T. Palenik
(74) *Attorney, Agent, or Firm* — Dentons US LLP

(57) ABSTRACT

Silicone gels are described that are adhesive to the skin. The gels can be used in particular for articles that are adhesive to the skin for medical or paramedical use.

20 Claims, No Drawings

SKIN-ADHESIVE SILICONE GEL

CROSS-REFERENCE TO PRIOR APPLICATIONS

This application is a National Stage of PCT/FR2017/000051, filed Mar. 16, 2017, and designating the United States (published on Sep. 21, 2017, as WO 2017/158250A1), which claims foreign priority under 35 U.S.C. § 119 to French Patent Application No. FR 1600444, filed Mar. 17, 2016, each hereby expressly incorporated by reference in its entirety and each assigned to the assignee hereof.

The present invention relates to a silicone gel that is of use in mammary prostheses, cushions and mattresses for preventing pressure sores or for use against the skin and more particularly:

- in an adhesive dressing which adheres to the skin, or part of such a dressing, in particular intended for non-traumatic removal on healthy skin and on a wound, or
- in a device for holding in place medical accessories, such as a device for attaching ostomy bags, or part of such a device, used in contact with the skin, of sensor, probe, catheter or needle type.

Silicone gels are conventionally obtained by crosslinking a composition comprising an organopolysiloxane bearing at least two vinyl functions per molecule, a polyorganohydrosiloxane bearing at least three SiH functions per molecule (called crosslinker"), a di(hydrosilyl)organopolysiloxane bearing two SiH functions (called "chain extender") and a platinum-based hydrosilylation catalyst. These silicone gels are conventionally used for the protection of electronic materials sensitive to vibrations, to impacts, to temperature and more generally to physical and chemical attacks from the ambient atmosphere. For the implementation in this application, silicone gels encapsulate the electronic components ("potting"). Silicone gels are also used as basic medical material, in particular for producing mammary prostheses or dressings. They are used as an adhesive, provided that their adherent properties are significant, and as an impact absorber material. For all these applications, the physical properties of these gels are adapted according to the use by varying the amounts of siloxyl units bearing Si-alkenyl (usually Si-vinyl) and SiH functions.

Thus, the majority of the silicone compositions which are precursors of silicone gels and which are currently sold are prepared from crosslinking silicone compositions by poly-addition reactions in which the RHAlk molar ratio=tH/tAlk≤1.0 and usually close to 0.8 with:

tH=number of moles of hydrogen atom directly bonded to a silicon atom of the organopolysiloxanes bearing SiH reactive functions, tAlk=number of moles of alkenyl directly bonded to a silicon atom of the organopolysiloxanes bearing alkenylated reactive functions.

Reference WO-2008/057155 describes compositions forming a silicone gel which have an average RHAlk of from 0.7 to 1.5, typically from 0.8 to 0.95 and with an average RHCE of from 0.4 to 1, typically 0.8 to 0.95. RHCE=(moles of hydrogen bonded to silicon by means of chain extenders)/(moles of hydrogen bonded to silicon). These gels are suitable for temporarily adhering a medical device to a biological substrate such as the skin. Silicone gels provide a high adhesion to the skin and a low force of release of the polyethylene substrate from the skin.

However, the reference EP-322118 describes silicone compositions which are precursors of silicone gels having rapid crosslinking kinetics, in which the RHAlk molar ratio ranges from 1 to 20. These silicone compositions which crosslink by hydrosilylation are characterized by an excess of SiH reactive functions with respect to Si-alkenyl functions. The silicone compositions described are limited to the compositions comprising:

- an organopolysiloxane having at least 3 SiH functions (acting as crosslinker),
- an organopolysiloxane having diorganohydrosiloxy ends (=a "chain extender" having 2 SiH functions),
- an organopolysiloxane having two Si-alkenyl functions per polymer and the kinematic viscosity of which at 25° C. is from 50 to 10 000 mm²·s.

The examples use silicone compositions having RHAlks of 3, 4, 7 and 10 with crosslinking polymers which contain 0.7% by weight of hydrogen atom originating from SiH functions, or 1.5% by weight of hydrogen atom originating from SiH functions, that is to say respectively 20% and 43% by weight of SiH functions per polymer.

However, the "tack" problem with respect to the skin is not dealt with by this reference. Indeed, in the medical or paramedical field, it is important for silicone gels to adhere well to the skin because they are also used as a means for attaching the item to the user's skin and for holding it in place in numerous medical devices. The skin-adhesion force of a silicone gel is evaluated by measuring the instantaneous "tack", which evaluates the capability of a silicone to rapidly adhere to the skin.

A method termed "Probe Tack" method is known for assessing and evaluating the tack, and is described in the standard ASTM D2979. This test makes it possible to measure the tack of the adhesive. The principle is the following for the silicone gels described in the present statement: a cylindrical punch with a flat face is brought into contact with the adhesive film which is deposited on the substrate. The punch is then kept in contact with the silicone gel for a contact time of one second at a constant pressure of 100 gf/cm². Next, the punch is detached from the gel at a constant speed of 10 mm/s, and the force required to separate the silicone gel from the rod is measured and expressed in gf/cm², while the detachment energy is expressed in mJ/cm². In the present report, when reference is made to the property of "tack" to the skin, this property is evaluated by the detachment energy of the gel tested. Thus, a silicone gel which has a "tack" (or detachment energy) of greater than or equal to 14 mJf/cm measured according to the conditions described above is a silicone gel that is particularly desired and suitable for use in medical devices in contact with the skin.

Medical devices intended to be in contact with the skin and using silicone gels are presently very widespread. This is because the intrinsic properties of silicone gels mean that they adhere to dry skin, but do not stick to the surface of a moist wound, consequently not causing any damage when they are removed. However, there is still a need to improve the instantaneous "tack" of silicone gels, if only to hold the medical device in place on the patient's skin.

Silicone gels also have the advantage of being able to be assembled to a large number of supports while at the same time being inert with respect to the organism, thus avoiding any problem of toxicity when they are used in human beings. Silicone gels are, inter alia, used for the treatment of wounds or scars because they provide the medical device with properties that facilitate recovery of the patient while maintaining a moist environment around the wound and thus make it possible to maintain the hydration of the damaged tissues. These properties are well documented and include the fact that silicone gels do not leave particles or fibers in the wound, are flexible on the skin and are comfortable.

Thus, numerous medical devices integrate silicone gels as adhesive to the skin or as layer in contact with a wound to be treated and, for these applications, the substrate must be biocompatible and flexible and have good mechanical properties. Polyurethane films are very widely used because they meet all these technical requirements, in particular:
- good biocompatibility,
- good permeability to water vapor (management of fluids between the dressing and the external medium in order to prevent the dressing from swelling or from detaching),
- good mechanical properties (tensile strength, elongation capacity),
- a soft feel, and
- good flexibility.

The use of these products involves a step of coating onto a substrate. The coating of the silicone gels onto these polyurethanes supports is a key step of the process for producing the medical device, and the properties of this composite must be good. Indeed, the gel must be sufficiently adhesive to the skin to hold the device in place and it must also sufficiently adhere to the substrate to avoid the generation of residues on removal of the device.

However, it is known that the adhesion of silicone gels on plastic supports having a low surface energy is difficult to obtain. However, the adhesion to the substrate is fundamental to ensure good cohesion of the adhesive item to the skin, in particular for a medical or paramedical use, and to avoid either the presence of residues on removal of the item, or the formation of an air pocket which is a source of folds when the gel is used in a mammary prosthesis comprising a plastic shell.

Thus, when silicone gels are used either as elements for coating plastic supports, for example made of polyurethane, or in a mammary prosthesis consisting of a plastic, for example polyurethane, pouch, it is desirable to reinforce their adhesion to the supports in such a way that the products using them no longer exhibit the problems described above.

In the face of this problem, it is known that the adhesion of silicone gels on a plastic substrate is improved by applying, to the surface of the support, a corona treatment in order to modify the surface energy of said support. This technique consists in oxidizing the surface of the material in order to improve the wettability by increasing the surface tension. However, the level of adhesion obtained is not always sufficient for some applications.

Another route for improving the adhesion of silicone gels to plastic, for example polyurethane, supports consists in using an adhesion primer, also known as "attachment primer". This technical approach makes it possible to obtain products which provide a slightly improved level of attachment compared with a polymeric substrate subjected to a corona treatment. Among the primers existing at the current time, mention may be made of:
- primers formulated in a solvent medium. An example is described in patent application WO 2011/092404 by the company Bluestar Silicones France, wherein a primer consists of an active material (organopolysiloxane comprising a hydrosilyl (SiH) and Si-alkenyl function or a silicone resin having hydrosilyl functions) diluted in a silicone solvent (cyclopentasiloxane). This primer is very effective, but must be used under very precise conditions (dilution of active material, weight of primer coated) so that a good balance of properties (adhesion to the substrate and preservation of the "tack") is achieved. Furthermore, another drawback of this type of primer is its solvent content which makes its use more difficult during the coating step; and
- silicone elastomer primers which are prepared from precursor compositions which crosslink via a hydrosilylation reaction comprising adhesion promoters which are usually silanes that make it possible to improve the adhesion on various substrates (polyamide, polyester or polyurethane substrates). However, during the preparation of the silicone elastomer, the condensation of the silanes releases by-products (alcohols) which make the use of this type of primer more difficult during the coating step.

It is also possible to use adhesion primers formulated in the aqueous phase, but the results in terms of improvement of adhesion are not satisfactory, and they also require the incorporation of additives (such as, for example, acetic acid) during the use thereof, and/or the application of heat treatment, said treatment being incompatible with the use of certain polymeric substrates.

According to another technical approach, for example described in patent application WO-2005/051442 from the company Dow Corning Corp., the adhesion of a silicone gel to the surface of a plastic polymeric substrate, such as polyurethane films, is improved by directly treating the substrate or the silicone gel by bringing into contact with derivatives: titanate, zirconate, siloxanes having hydrosilyl functions or platinum, such as a platinum (0)-1,3-diethenyl-1,1,3,3-tetramethyldisiloxane complex. It should be noted that the use of adhesion primers of titanate type, such as titanium tetrabutanoate, is very widespread but poses problems during the use thereof.

A solution to the problem stated above is set out in the patent application WO 2014/131999 from the company Urgo, which describes an item comprising at least one polymeric substrate assembled to at least one silicone polymer layer, characterized in that at least one of the polymeric substrate or of the silicone polymer layer has been brought into contact with the titanium dioxide, magnesium oxide and/or zinc oxide particles, before assembly of said item, and in that at least one of the polymeric substrate or of the silicone polymer layer has been brought into contact with water before or after assembling said item. The adhesion results show an improvement compared with a corona treatment or with the impregnation of a non-woven support based on polyethylene impregnated with titanium tetrabutanoate at 5% by weight in isopropanol.

Thus, the use of adhesion primers of different types or of adhesion promoters of titanate or silane type in the silicone gels causes a large number of problems or complications linked to the processing thereof and to the use thereof. In addition, the adhesion levels obtained with these treatments also need to be improved.

The applicant has thus sought to develop a novel silicone gel which provides improved adhesion between a silicone gel and a plastic film, for example a polyurethane film or polyester film, not using adhesion promoters of titanate or silane type, nor even solvent type, and providing the best possible guarantees in terms of health safety.

In this state of knowledge, one of the essential objectives of the present invention is to provide a silicone composition which, after crosslinking, provides a silicone gel having:
- good adhesion on plastics, for example polyester materials or polyurethane materials, and
- good adhesion (or "tack") on the skin, that is to say a silicone gel having an instantaneous adhesion (or "tack") greater than or equal to 14 mJ/cm measured according to the conditions described above.

Another object of the present invention is to provide novel items which adhere to the skin, comprising a silicone gel according to the invention having good "tack" properties.

These objectives are achieved by the invention which relates to a silicone composition A which is a precursor of a silicone gel G and which is crosslinkable by hydrosilylation comprising:

1) at least one organopolysiloxane B comprising:
   (i) at least two siloxyl units of formula (B1):

$$(Y)_a(Z)_b SiO_{(4-(a+b))/2} \quad \text{(B1)}$$

in which:
   Y represents a monovalent radical containing from 2 to 6 carbon atoms, having at least one alkenyl group;
   Z represents a monovalent radical containing from 1 to 20 carbon atoms and not comprising an alkenyl group;
   a and b represent integers, a being 1, 2 or 3, b being 0, 1 or 2 and (a+b) being 1, 2 or 3;
   (ii) and optionally comprising other siloxyl units of formula (B2):

$$(Z)_c SiO_{(4-c)/2} \quad \text{(B2)}$$

in which:
   Z has the same meaning as above, and
   c represents an integer which is 0, 1, 2 or 3, 2) at least one organopolysiloxane CE comprising:
   two siloxyl end units, which may be identical or different, of formula (CE-1):

$$(H)_p(R^1)_q SiO_{1/2} \quad \text{(CE-1)}$$

in which:
   the symbol $R^1$ corresponds to a $C_1$ to $C_8$ alkyl group or to a $C_6$ to $C_{10}$ aryl group;
   and the symbol H represents a hydrogen atom, with p=0 or 1, q=2 or 3 and (p+q)=3;
   at least one siloxyl unit of formula (CE-2):

$$(H)_n(R^2)_m SiO_{2/2} \quad \text{(CE-2)}$$

in which the radical $R^2$ corresponds to a $C_1$ to $C_8$ alkyl group or a $C_6$ to $C_{10}$ aryl group, the symbol H represents a hydrogen atom and with n=0 or 1, m=1 or 2 and (n+m)=2, and
   with the condition according to which the organopolysiloxane CE contains two hydrogen atoms each one bonded to a different silicon atom per polymer, and preferably the organopolysiloxane CE contains, per polymer, two siloxyl units of formula (CE-1) in which p=1 and at least one siloxyl unit of formula (CE-2) in which n=0;

3) at least one organopolysiloxane XL comprising:
   at least three siloxyl units of formula (XL-1):

$$(H)(L)_e SiO_{(3-e)/2} \quad \text{(XL-1)}$$

in which the symbol H represents a hydrogen atom, the symbol L represents an alkyl having from 1 to 8 carbon atoms inclusive or a $C_6$ to $C_{10}$ aryl, and the symbol e is equal to 0, 1 or 2; and
   optionally other siloxyl units of formula (XL-2):

$$(L)_g SiO_{(4-g)/2} \quad \text{(XL-2)}$$

in which the symbol L represents an alkyl having from 1 to 8 carbon atoms inclusive or a $C_6$ to $C_{10}$ aryl and the symbol g is equal to 0, 1, 2 or 3, and
   with the condition according to which the organopolysiloxane XL contains between 15.1% and 40.0% by weight of Si—H function per polymer, and preferably between 18% and 35.0% by weight of Si—H function per polymer, 4) an effective amount of at least one hydrosilylation catalyst E, 5) at least one hydrosilylation reaction inhibitor D, 6) optionally at least one additive K, and the weight amounts of the organopolysiloxanes B, CE and XL are chosen so as to satisfy the following three conditions:
   a) the molar ratio RHAlk=tH/tAlk≥3.0, preferably 3.0≤RHAlk≤24 and even more preferentially between 4.5≤RHAlk≤20;
   b) the molar ratio $RH^{CE}V=nH^{CE}/tAlk≥4.50$ and preferably $4.50≤RH^{CE}V≤20$, and
   c) the mol % $RH^{CE}=(nH^{CE/tH})\times 100$ is greater than or equal to 90 mol %, and preferably between 90 mol % and 95 mol %, with:
      tH=number of moles of hydrogen atom directly bonded to a silicon atom of the organopolysiloxanes CE and XL,
      tAlk=number of moles of alkenyl directly bonded to a silicon atom of the organopolysiloxane B; and
      $nH^{CE}$=number of moles of hydrogen atom directly bonded to a silicon atom of the organopolysiloxane CE.

The applicant has implemented considerable research means and numerous experiments to achieve this objective among others. At the end of this, to its credit, it found, entirely surprisingly and unexpectedly, in order to obtain a silicone gel having good adhesion to a plastic support (for example polyurethane support) and good "tack" to the skin (greater than or equal to 14 mJ/cm measured according to the conditions described above), it is sufficient to use silicone compositions which crosslink via hydrosilylation reactions, comprising organopolysiloxanes XL having a specific SiH function content of between 15.1% and 40.0% by weight of Si—H function per polymer, preferably between 18% and 35.0% by weight of Si—H function per polymer, and that the choice of the constituents is determined so as to adhere to the following conditions
   a) the molar ratio RHAlk=tH/tAlk≥3.0,
   b) the molar ratio $RH^{CE}V=nH^{CE}/tAlk≥4.50$, and
   c) the mol % $RH^{CE}=(nH^{CE}/tH)\times 100$ is greater than or equal to 90 mol %, and preferably between 90 mol % and 95 mol %.

For the purposes of the present invention, the expression "silicone gel" denotes a crosslinked silicone product which exhibits no flow when it is in the stable state and which is characterized in particular by a degree of penetration (or "penetrability") of between 80 and 300 tenths of one mm. It is measured by penetrometry according to the standard NF ISO 2137, using a Petrotest penetrometer, model PNR 12, with a total weight of the rod and cone fixed at 62.5 g. The cone penetrability of a silicone gel is determined at 25° C. by measuring the depth of penetration of the cone into the sample, said depth being obtained by releasing the cone assembly of the penetrometer and leaving the cone to act for 5 seconds.

According to one particular embodiment of the silicone composition A:
   the organopolysiloxane B has a dynamic viscosity at 25° C. of between 100 mPa·s and 120 000 mPa·s,
   the organopolysiloxane CE has a dynamic viscosity at 25° C. of between 1 mPa·s and 500 mPa·s, and preferably between 5 and 200 mPa·s, and the organopolysiloxane XL has a dynamic viscosity at 25° C. of between 5 mPa·s and 2000 mPa·s, and preferably between 5 and 500 mPa·s.

All the viscosities under consideration in the present description correspond to a "Newtonian" dynamic viscosity magnitude at 25° C., i.e. the dynamic viscosity which is measured, in a manner that is known per se, with a Brookfield viscometer at a shear rate gradient that is low enough for the measured viscosity to be independent of the rate gradient.

According to one advantageous embodiment, the nature and the weight amounts of the organopolysiloxanes B, CE and XL are chosen such that the dynamic viscosity at 25° C. of the silicone composition A is between 200 mPa·s and 100 000 mPa·s, and preferably between 200 mPa·s and 80 000 mPa·s.

According to the invention, it is advantageous to adhere to the following two conditions:
the organopolysiloxane CE has at least 5 silicon atoms and a ratio: (number of moles of SiH group)/(total number of silicon atoms) of between 0.05 and 0.40, and preferably of between 0.08 and 0.35, and
the organopolysiloxane XL has at least 5 silicon atoms and a ratio: (number of moles of SiH group)/(total number of silicon atoms) of between 0.35 and 0.80, and preferably of between 0.35 and 0.75.

According to another particular embodiment, the silicone composition A according to the invention comprises at least two organopolysiloxanes B comprising, per molecule, at least two $C_2$ to $C_6$ alkenyl radicals each bonded to a silicon atom, the first having a dynamic viscosity at 25° C. of between 50 000 mPa·s and 120 000 mPa·s, and the second having a dynamic viscosity at 25° C. of between 500 mPa·s and 20 000 mPa·s.

According to the invention, it is judicious that, for definition of the organopolysiloxane B in the formula (B1), the symbol a can preferably be equal to 1 or 2, and even more preferentially 1. Furthermore, in formula (B1) and in formula (B2), the symbol Z may preferentially represent a monovalent radical chosen from the group formed by an alkyl group containing 1 to 8 carbon atoms, optionally substituted with at least one halogen atom, and a $C_6$ to $C_{10}$ aryl group. Z may advantageously represent a monovalent radical chosen from the group formed by: methyl, ethyl, propyl, 3,3,3-trifluoropropyl, xylyl, tolyl and phenyl. In addition, in formula (B1), the symbol Y may advantageously represent a radical chosen from the group consisting of vinyl, propenyl, 3-butenyl and 5-hexenyl. Preferably, the symbol Y is a vinyl and the symbol Z is a methyl.

The organopolysiloxane B may have a linear, branched, cyclic or network structure. When they are linear organopolysiloxanes, they can essentially consist:
of siloxyl units "D" chosen from the units of formulae $(Y)_2SiO_{2/2}$, $(Y)(Z)SiO_{2/2}$ and $(Z)_2SiO_{2/2}$; and
of siloxyl units "M" chosen from the units of formulae $(Y)_3SiO_{1/2}$, $(Y)_2(Z)SiO_{1/2}$, $(Y)(Z)_2SiO_{1/2}$ and $(Z)_3SiO_{2/2}$,
in which formulae, the symbols Y and Z are as defined above.

By way of example of units "D", mention may be made of dimethylsiloxy, methylphenylsiloxy, methylvinylsiloxy, methylbutenylsiloxy, methylhexenylsiloxy, methyldecenylsiloxy and methyldecadienylsiloxy groups.

By way of example of units "M", mention may be made of trimethylsiloxy, dimethylphenylsiloxy, dimethylvinylsiloxy and dimethylhexenylsiloxy groups.

The organopolysiloxane B, in particular when it is linear, can be a silicone oil having a dynamic viscosity at 25° C. of between 50 mPa·s and 120 000 mPa·s, and preferentially between 100 mPa·s and 120 000 mPa·s.

When the organopolysiloxane B is cyclic, it can consist of siloxyl units "D" chosen from the units of formulae $Y_2SiO_{2/2}$, $YZSiO_{2/2}$ and $Z_2SiO_{2/2}$. Examples of such units "D" are described above. This cyclic organopolysiloxane can have a dynamic viscosity at 25° C. of between 1 mPa·s and 5000 mPa·s.

As examples of organopolysiloxane B that are of use, mention may be made of:
polydimethylsiloxanes comprising dimethylvinylsilyl end groups;
poly(methylphenylsiloxane-co-dimethylsiloxane)s comprising dimethylvinylsilyl end groups;
poly(vinylmethylsiloxane-co-dimethylsiloxane)s comprising dimethylvinylsilyl end groups;
poly(dimethylsiloxane-co-vinylmethylsiloxane)s comprising trimethylsilyl end groups;
and cyclic polymethylvinylsiloxanes.

The organopolysiloxanes B which are polydimethylsiloxanes comprising dimethylvinylsilyl end groups having a dynamic viscosity at 25° C. of between 50 mPa·s and 120 000 mPa·s, and preferably of between 100 mPa·s and 80 000 mPa·s, are particularly advantageous. The organopolysiloxanes B which are particularly advantageous are those of formule $M^{Vi}D_xM^{Vi}$ in which:
Mn=siloxyl unit of formula: $(vinyl)(CH_3)_2SiO_{1/2}$
D=siloxyl unit of formula: $(CH_3)_2SiO_{2/2}$, and
x is a number between 1 and 1000, and preferably between 5 and 1000.

As examples of organopolysiloxane CE which has a "chain extender" function, mention may be made of polydimethylsiloxanes comprising dimethylhydrosilyl end groups having a dynamic viscosity at 25° C. of between 1 mPa·s and 500 mPa·s, preferably of between 5 mPa·s and 200 mPa·s, even more preferentially of between 1 and 30 mPa·s. Particularly advantageous organopolysiloxanes CE are poly(dimethylsiloxy)α,ω(dimethylhydrosiloxys of formula $M^HD_xM^H$ in which:
$M^H$=siloxyl unit of formula: $(H)(CH_3)_2SiO_{1/2}$
D=siloxyl unit of formula: $(CH_3)_2SiO_{2/2}$, and
x is an integer between 1 and 200, preferably between 1 and 150 and even more preferentially between 3 and 120.

The organopolysiloxane CE is described as "chain extender" since it has the presumed effect of increasing the mesh size of the network during the crosslinking. When the SiH reactive functions are at the chain end, the term "telechelic" is sometimes preferred to the term "chain extender".

As organopolysiloxane XL which has a crosslinking function and which is of use according to the invention, mention may be made of those of formulae $M^HD_xD_w^HM^H$, $M^HD_xD_y^H M$ and $M D_xD_z^H M$, in which formulae:
$M^H$=siloxyl unit of formula: $(H)(CH_3)_2SiO_{1/2}$
$D^H$=siloxy unit of formula: $(H)(CH_3)_2SiO_{2/2}$
D=siloxyl unit of formula: $(CH_3)_2SiO_{2/2}$, and
M=siloxyl unit of formula: $(CH_3)_3SiO_{1/2}$,
with:
x is a number between 0 and 500, preferably between 2 and 250 and even more preferentially between 5 and 40;
w is a number between 1 and 500, preferably between 1 and 250 or between 1 and 100 and even more preferentially between 1 and 70;

y is a number between 2 and 500, preferably between 3 and 250 or between 2 and 100 and even more preferentially between 2 and 70; and z is a number between 3 and 500, preferably between 3 and 250 or between 3 and 100 and even more preferentially between 3 and 70, and with the condition that the organopolysiloxane XL contains between 15.1% and 40.0% by weight of Si—H function per polymer, and preferably between 18% and 35.0% by weight of Si—H function per polymer.

As hydrosilylation catalyst E that is useful according to the invention, mention may be made of the compounds of a metal belonging to the group of platinum which is well known to those skilled in the art. The metals of the platinum group are those known as platinoids, a name which groups together, in addition to platinum, ruthenium, rhodium, palladium, osmium and iridium. The compounds of platinum and of rhodium are preferably used. Use may in particular be made of the complexes of platinum and of an organic product described in U.S. Pat. Nos. 3,159,601, 3,159,602 and 3,220,972 and European patents EP-A-0 057 459, EP-A-0 188 978 and EP-A-0 190 530, and the complexes of platinum and of vinyl organosiloxanes described in U.S. Pat. No. 3,419,593. The catalyst generally preferred is platinum. By way of examples, mention may be made of black platinum, chloroplatinic acid, a chloroplatinic acid modified with an alcohol, a complex of chloroplatinic acid with an olefin, an aldehyde, a vinylsiloxane or an acetylenic alcohol, among others. The Karstedt solution or complex, as described in U.S. Pat. No. 3,775,452, chloroplatinic acid hexahydrate or a platinum catalyst comprising carbene ligands is preferred.

As hydrosilylation reaction inhibitor D that is useful according to the invention, mention may be made of the one chosen from α-acetylenic alcohols, α-α'-acetylenic diesters, ene-yne conjugated compounds, α-acetylenic ketones, acrylonitriles, maleates, fumarates and mixtures thereof. These compounds capable of performing the hydrosilylation inhibitor function are well known to those skilled in the art. They can be used alone or as mixtures.

An inhibitor D of α-acetylenic alcohol type can be chosen from the compounds of following formula (D1):

$$(R^1)(R^2)C(OH)-C\equiv CH \quad (D1)$$

in which:
the group $R^1$ represents an alkyl group, a cycloalkyl group, a (cycloalkyl)alkyl group, a $C_6$ to $C_{10}$ aryl group or a $C_7$ to $C_{18}$ arylalkyl group,
the group $R^2$ represents a hydrogen atom, an alkyl group, a cycloalkyl group, a (cycloalkyl)alkyl group, a $C_6$ to $C_{10}$ aryl group or a $C_7$ to $C_{18}$ arylalkyl group,
or else $R^1$ and $R^2$ constitute, together with the carbon atom to which they are bonded, a 5-, 6-, 7- or 8-membered aliphatic ring, optionally substituted one or more times.

According to formula (D1):
the term "alkyl" is intended to mean a saturated hydrocarbon-based chain containing from 1 to 20 carbon atoms and preferably from 1 to 8 carbon atoms. An alkyl group may be chosen from the group consisting of methyl, ethyl, isopropyl, n-propyl, tert-butyl, isobutyl, n-butyl, n-pentyl, isoamyl and 1,1-dimethylpropyl groups;
the term "cycloalkyl" is intended to mean according to the invention a saturated monocyclic or polycyclic, preferably monocyclic or bicyclic, hydrocarbon-based group containing from 3 to 20 carbon atoms, preferably from 5 to 8 carbon atoms.

When the cycloalkyl group is polycyclic, the multiple cyclic nuclei may be attached to each other via a covalent bond and/or via a spirane atom and/or may be fused with each other. A cycloalkyl group may be chosen from the group consisting of cyclopropyl, cyclobutyl, cyclopentyl, cyclohexyl, cycloheptyl, cyclooctyl, adamantane and norbornane;
the term "(cycloalkyl)alkyl" is intended to mean according to the invention a cycloalkyl group as defined above bonded to an alkyl group also as defined above;
the term "aryl" is intended to mean according to the invention a monocyclic or polycyclic aromatic hydrocarbon-based group containing from 6 to 10 carbon atoms.

An aryl group may be chosen from the group consisting of phenyl, naphthyl and anthracenyl;
the term "arylalkyl" is intended to mean according to the invention an aryl group as defined above bonded to an alkyl group also as defined above.

According to one preferred embodiment, in formula (D1), $R^1$ and $R^2$ constitute, together with the carbon atom to which they are bonded, an unsubstituted 5-, 6-, 7- or 8-membered aliphatic ring. According to another preferred embodiment, $R^1$ and $R^2$, which may be identical or different, represent, independently of one another, a $C_1$ to $C_{12}$, preferably $C_1$ to $C_6$, monovalent alkyl group.

An inhibitor D which is an α-acetylenic alcohol that is useful according to the invention can be chosen from the group consisting of the following compounds: 1-ethynyl-1-cyclopentanol; 1-ethynyl-1-cyclohexanol (also called ECH); 1-ethynyl-1-cycloheptanol; 1-ethynyl-1-cyclooctanol; 3-methyl-1-butyn-3-ol (also called MBT); 3-methyl-1-pentyn-3-ol; 3-methyl-1-hexyn-3-ol; 3-methyl-1-heptyn-3-ol; 3-methyl-1-octyn-3-ol; 3-methyl-1-nonyn-3-ol; 3-methyl-1-decyn-3-ol; 3-methyl-1-dodecyn-3-ol; 3-methyl-1-pentadecyn-3-ol; 3-ethyl-1-pentyn-3-ol; 3-ethyl-1-hexyn-3-ol; 3-ethyl-1-heptyn-3-ol; 3,5-dimethyl-1-hexyn-3-ol; 3-isobutyl-5-methyl-1-hexyn-3-ol; 3,4,4-trimethyl-1-pentyn-3-ol; 3-ethyl-5-methyl-1-heptyn-3-ol; 3,6-diethyl-1-nonyn-3-ol; 3,7,11-trimethyl-1-dodecyn-3-ol (also called TMDDO); 1,1-diphenyl-2-propyn-1-ol; 3-butyn-2-ol; 1-pentyn-3-ol; 1-hexyn-3-ol; 1-heptyn-3-ol; 5-methyl-1-hexyn-3-ol; 4-ethyl-1-octyn-3-ol and 9-ethynyl-9-fluorenol.

An inhibitor D of α,α'-acetylenic diester type can be chosen from the compounds of formula (D2) below:

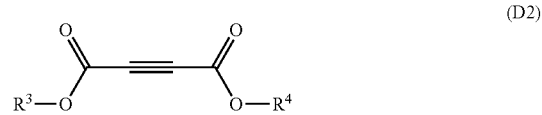

(D2)

in which the groups $R^3$ and $R^4$, which may be identical or different, represent, independently of one another, an alkyl group, a cycloalkyl group, a (cycloalkyl)alkyl group, a $C_6$ to $C_{10}$ aryl group, a $C_7$ to $C_{18}$ arylalkyl group or a silyl group.

The term "silyl" is intended to mean according to the invention a group of formula—$SiR_3$, in which each symbol R independently represents an alkyl group containing from 1 to 20 carbon atoms, preferably from 1 to 8 carbon atoms. A silyl group can for example be the trimethylsilyl group.

According to one particular embodiment, in formula (D2), $R^3$ and $R^4$, which may be identical or different, independently of one another represent a $C_1$ to $C_{12}$, preferably $C_1$ to $C_6$, alkyl group or the trimethylsilyl group. An inhibitor D which is an α-α'-acetylenic diester that is useful according to the invention can be chosen from the group consisting of the following compounds: dimethyl acetylenedicarboxylate (DMAD), diethyl acetylenedicarboxylate, tert-butyl acetylenedicarboxylate and bis(trimethylsilyl) acetylenedicarboxylate.

An inhibitor D of ene-yne conjugated compound type can be chosen from the compounds of formula (D3) below:

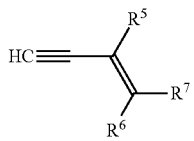
(D3)

in which:
the groups $R^5$, $R^6$ and $R^7$ represent, independently of one another, a hydrogen atom, an alkyl group, a cycloalkyl group, a (cycloalkyl)alkyl group, a $C_6$ to $C_{10}$ aryl group or a $C_7$ to $C_{18}$ arylalkyl group,
or else at least two groups among the groups $R^5$, $R^6$ and $R^7$ constitute, together with the carbon atom or atoms to which they are bonded, a 5-, 6-, 7- or 8-membered aliphatic ring, optionally substituted one or more times.

According to one particular embodiment, the groups $R^5$, $R^6$ and $R^7$ represent, independently of one another, a hydrogen atom, a $C_1$ to $C_{12}$, preferably $C_1$ to $C_6$, alkyl group or a $C_6$ to $C_{10}$ aryl group. An inhibitor D which is an ene-yne conjugated compound that is useful according to the invention can be chosen from the group consisting of the following compounds: 3-methyl-3-penten-1-yne; 3-methyl-3-hexen-1-yne; 2,5-dimethyl-3-hexen-1-yne; 3-ethyl-3-buten-1-yne; and 3-phenyl-3-buten-1-yne. According to another particular embodiment, two groups chosen from the groups $R^5$, $R^6$ and $R^7$ constitute, together with the carbon atom(s) to which they are bonded, an unsubstituted 5-, 6-, 7- or 8-membered aliphatic ring and the remaining third group represents a hydrogen atom or a $C_1$ to $C_{12}$, preferably $C_1$ to $C_6$, alkyl group. An inhibitor D which is an ene-yne conjugated compound useful according to the invention may be 1-ethynyl-1-cyclohexene.

An inhibitor D of α-acetylenic ketone type can be chosen from the compounds of formula (D4) below:

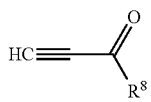
(D4)

in which: $R^8$ represents an alkyl group, a cycloalkyl group, a (cycloalkyl)alkyl group, a $C_6$ to $C_{10}$ aryl group or a $C_7$ to $C_{18}$ arylalkyl group, it being possible for the alkyl, cycloalkyl, (cycloalkyl)alkyl, aryl or arylalkyl groups to optionally be substituted one or more times with a chlorine, bromine or iodine atom.

According to one preferred embodiment, $R^8$ represents a $C_1$ to $C_{12}$, preferably $C_1$ to $C_6$, monovalent alkyl group, optionally substituted one or more times with a chlorine or bromine atom, or a cycloalkyl group, or a $C_6$ to $C_{10}$ aryl group. An inhibitor D which is an α-acetylenic ketone that is useful according to the invention can be chosen from the group consisting of the following compounds: 1-octyn-3-one, 8-chloro-1-octyn-3-one; 8-bromo-1-octyn-3-one; 4,4-dimethyl-1-octyn-3-one; 7-chloro-1-heptyn-3-one; 1-hexyn-3-one; 1-pentyn-3-one; 4-methyl-1-pentyn-3-one; 4,4-dimethyl-1-pentyn-3-one; 1-cyclohexyl-1-propyn-3-one; benzoacetylene and o-chlorobenzoylacetylene.

An inhibitor D of acrylonitrile type can be chosen from the compounds of formula (D5) below:

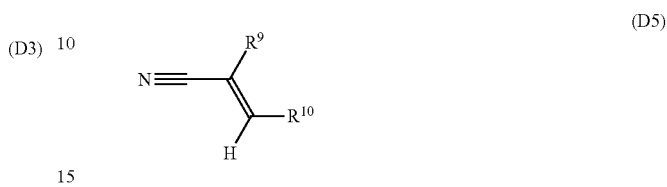
(D5)

in which: $R^9$ and $R^{10}$ represent, independently of one another, a hydrogen atom, a chlorine, bromine or iodine atom, an alkyl group, a cycloalkyl group, a (cycloalkyl)alkyl group, a $C_6$ to $C_{10}$ aryl group or a $C_7$ to $C_{16}$ arylalkyl group, it being possible for the alkyl, cycloalkyl, (cycloalkyl)alkyl, aryl or arylalkyl groups to optionally be substituted one or more times with a chlorine, bromine or iodine atom.

An inhibitor D which is an acrylonitrile that is useful according to the invention can be chosen from the group consisting of the following compounds: acrylonitrile; methacrylonitrile; 2-chloroacrylonitrile; crotonitrile and cinnamonitrile.

An inhibitor D of maleate or fumarate type can be chosen from the compounds of formulae (D6) and (D7) below:

(D6)

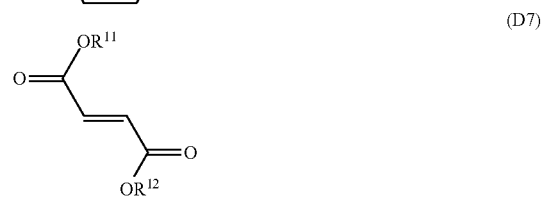
(D7)

in which: $R^{11}$ and $R^{12}$, which may be identical or different, represent, independently of one another, an alkyl or alkenyl group, a cycloalkyl group, a (cycloalkyl)alkyl group, a $C_6$ to $C_{10}$ aryl group or a $C_7$ to $C_{16}$ arylalkyl group, said alkyl, alkenyl, cycloalkyl, (cycloalkyl)alkyl, aryl and arylalkyl groups possibly being substituted with an alkoxy group.

The term "alkenyl" is intended to mean according to the invention a saturated hydrocarbon-based chain containing from 2 to 6 carbon atoms, and comprising at least one double unsaturation. Preferably, the alkenyl group is chosen from the group consisting of a vinyl or an allyl.

The term "alkoxy" is intended to mean, according to formula (D6) or (D7), an alkyl group as defined above bonded to an oxygen atom. An alkoxy group can be chosen from the group consisting of methoxy, ethoxy, propoxy and butoxy.

According to one particular embodiment, $R^{11}$ and $R^{12}$, which may be identical or different, represent, independently of one another, a $C_1$ to $C_{12}$, preferably $C_1$ to $C_6$, alkyl or alkenyl group optionally substituted with a $C_1$ to $C_6$ alkoxy group.

An inhibitor D which is a maleate or a fumarate that is useful according to the invention can be chosen from the group consisting of diethyl fumarate, diethyl maleate, diallyl fumarate, diallyl maleate and bis(methoxyisopropyl) maleate.

Inhibitors D chosen from α-acetylenic alcohols, α-α'-acetylenic diesters, ene-yne conjugated compounds, α-acetylenic ketones, acrylonitriles, maleates and fumarates are commercially available. Mention may in particular be made of ECH (1-ethynyl-1-cyclohexanol) which is commercially available from BASF, dimethyl maleate which is commercially available from DMS and dimethyl acetylenedicarboxylate which is commercially available from City Chemical LLC.

These inhibitors are added in a weight amount of between 1 and 50 000 ppm relative to the weight of the total silicone composition, in particular between 10 and 10 000 ppm, preferably between 20 and 2000 ppm and even more preferentially between 20 ppm and 500 ppm.

As an example of an additive K, mention may for example be made of a stabilizer derived from the family of silylated derivatives of phosphoric acid, such as silylated esters of phosphoric acid.

Particularly advantageous results are obtained when the silicone composition A comprises:
1) at least one organopolysiloxane B which is a polydimethylsiloxane comprising dimethylvinylsilyl end groups having a dynamic viscosity at 25° C. of between 50 mPa·s and 120 000 mPa·s, and preferably of between 100 mPa·s and 80 000 mPa·s and having a formula $M^{Vi}D_xM^{Vi}$, with:
   $M^{Vi}$=siloxyl unit of formula: $(vinyl)(CH_3)_2SiO_{1/2}$
   D=siloxyl unit of formula: $(CH_3)_2SiO_{2/2}$, and
   x is a number between 0 and 1000, and preferably between 5 and 1000,
2) at least one organopolysiloxane CE of formula $M^HD_xM^H$ with:
   $M^H$=siloxyl unit of formula: $(H)(CH_3)_2SiO_{1/2}$
   D=siloxyl unit of formula: $(CH_3)_2SiO_{2/2}$, and
   x is a number between 1 and 100, preferably between 1 and 150 and even more preferentially between 3 and 30,
3) at least one organopolysiloxane XL of formula $M^H D_x D_w^H M^H$, $M^H D_x D_y^H M$ or $M D_x D_z^H M$, in which formula:
   $M^H$=siloxyl unit of formula: $(H)(CH_3)_2SiO_{1/2}$
   $D^H$=siloxy unit of formula: $(H)(CH_3)SiO_{2/2}$
   D=siloxyl unit of formula: $(CH_3)_2SiO_{2/2}$, and
   M=siloxyl unit of formula: $(CH_3)_3SiO_{1/2}$,
with:
   x is a number between 0 and 500, preferably between 2 and 250 and even more preferentially between 5 and 80;
   w is a number between 1 and 500, preferably between 1 and 250 or between 1 and 100 and even more preferentially between 1 and 70;
   y is a number between 2 and 500, preferably between 3 and 250 or between 2 and 100 and even more preferentially between 2 and 70; and
   z is a number between 3 and 500, preferably between 3 and 250 or between 3 and 100 and even more preferentially between 3 and 70,
4) at least one hydrosilylation catalyst E,
5) at least one hydrosilylation reaction inhibitor D,
6) optionally at least one additive K, et
with the condition that the organopolysiloxane XL contains between 15.1% and 40.0% by weight of Si—H function per polymer, and preferably between 18% and 35.0% by weight of Si—H function per polymer, and the weight amounts of the organopolysiloxanes B, CE and XL are chosen so as to satisfy the following three conditions:
a) the molar ratio $RHAlk=tH/tAlk\geq 3.0$, preferably $3.0\leq RHAlk\leq 24$ and even more preferentially between $4.5\leq RHAlk\leq 20$;
b) the molar ratio $RH^{CE}=nH^{CE}/tAlk\geq 4.50$ and preferably $4.50\leq RH_{CE}V\leq 20$, and
c) the mol % $RH^{CE}=(nH^{CE}/tH)\times 100$ is greater than or equal to 90%, and preferably between 90% and 95%, with:
tH=number of moles of hydrogen atom directly bonded to a silicon atom of the organopolysiloxanes CE and XL,
tAlk=number of moles of alkenyl directly bonded to a silicon atom of the organopolysiloxane B; and
$nH^{CE}$=number of moles of hydrogen atom directly bonded to a silicon atom of the organopolysiloxane CE.

Another subject of the invention relates to a silicone gel G obtained by crosslinking of the composition A according to the invention and as defined above, preferably by heating at a temperature of between 70° C. and 200° C. and/or under the action of infrared radiation.

The silicone gel G has the advantage of adhering perfectly to a support, for example a polyurethane support, and of having good "tack" to the skin (or) that is to say it has a detachment energy value of $\geq 14$ mJ/cm$^2$.

Another subject of the invention relates to the use of the silicone gel G according to the invention and as defined above, in medical devices such as a mammary prosthesis, a dressing which adheres to the skin or a device for holding in place medical accessories used in contact with the skin, of sensor, probe, catheter or needle type.

Another subject of the invention relates to an item which adheres to the skin, comprising a substrate S which is a plastic film, preferably a polyester or polyurethane film, continuously or discontinuously coated onto at least one of the two faces with a silicone gel G according to the invention and as defined above.

Thus, in one preferred embodiment, the silicone composition A is continuously coated onto at least one of the two faces of said substrate S in a proportion of an amount of between 20 and 500 g/m$^2$, preferably of between 40 and 350 g/m$^2$ and even more preferentially of between 80 and 250 g/m$^2$, before being crosslinked, preferably by heating at a temperature of between 70° C. and 200° C. and/or under the action of infrared radiation, so as to obtain said item which adheres to the skin.

Preferably, the substrate S is a perforated flexible polyurethane film or a continuous flexible polyurethane film. This flexible polyurethane film can be produced from blown molten polyurethane.

Preferentially, a transparent or translucent flexible polyurethane film is used. When the adhesive item has a use as a dressing, the use of a transparent or translucent film has the advantage of making it possible to observe the wound, the injury or the site of entry of a catheter on which the dressing must be centered.

Preferably, said substrate S is a flexible polyurethane film having a thickness of from 5 to 600 μm, preferably from 5 to 250 μm and even more preferentially from 10 to 100 μm. As an example of a flexible polyurethane film, mention may be made of those which are used in the dressings sold by the company Smith & Nephew under the brand name Opsite®, or by the company 3M under the brand name Tegaderm® or else by Laboratoires URGO under the brand name Optiskin®. These dressings consist of a transparent adhesive thin polyurethane film (of about 20 to 50 μm). Their transparency allows visual verification of the area to be treated. As another example of a flexible polyurethane film, mention may also be made of those sold under the brand names Platilon® by the company Bayer Material Science and Inspire® by the company Coveris Advanced Coatings.

According to one preferred embodiment, said substrate S is a continuous flexible polyurethane film which is permeable to air and impermeable to fluids. This flexible polyurethane film may have a moisture vapor transmission rate (MVTR) which is variable according to the intended application. A technique for measuring the moisture vapor transmission rate in liquid contact is described in the standard NF-EN 13726-2. Preferably, the flexible polyurethane film will be chosen so as to obtain a dressing having a moisture vapor transmission rate (MVTR) greater than 300 g/m$^2$/24 hours, preferably greater than or equal to 600 g/m$^2$/24 hours, more preferably greater than or equal to 1000 g/m$^2$/24 hours.

According to another particular embodiment, the invention relates to an item which adheres to the skin, characterized in that the substrate S is a continuous flexible polyurethane film which comprises one top face S1 coated with the silicone gel G according to the invention and as defined above and one bottom face S2 on to which is affixed a pressure-sensitive adhesive. According to one advantageous variant of the invention, the continuous flexible polyurethane film is perforated so as to be able to promote exudate circulation.

Thus, the adhesive item according to the invention is, according to one particular embodiment, a removable adhesive laminate and has the advantage of being able to be used as a contact layer in contact with the skin in various types of dressings.

The pressure-sensitive adhesive can be any of the numerous pressure-sensitive adhesives known from the art. These adhesives, generally in an anhydrous and solvent-free form, are permanently adhesive at ambient temperature and adhere firmly to a variety of dissimilar surfaces during simple contact, without the need to use more than the pressure of a finger or the hand. They do not require activation by water, solvent or heat in order to have a strong maintaining adhesive force. Examples of pressure-sensitive adhesives comprise rubber/resin adhesives, which are mixtures of rubber material and of hard resin, and acrylic (or acrylate) adhesives. The class of pressure-sensitive adhesives that is currently preferred for use in the present invention is that of the acrylic adhesives.

Another subject of the invention therefore relates to a dressing or patch for medical or paramedical use, comprising an item which adheres to the skin according to the invention and as described above.

Preferably, the amounts of silicone composition A will be determined so as to obtain coatings having a silicone gel G content of between 20 and 500 g/m$^2$ of support, preferably between 40 and 350 g/m$^2$ and even more preferentially between 80 and 250 g/m$^2$.

As technique for depositing the silicone composition A, mention may for example be made of the coating techniques carried out using a knife, in particular a knife-over-roll, a floating knife or a knife-over-blanket, or by padding, that is to say by squeezing between two rolls, or else by lick roll, rotary machine, reverse roll, transfer, spraying.

As other coating technique, mention may be made of the curtain coating technique. Curtain coating is a process for applying a coating liquid to an item or a support. Curtain coating is characterized by the formation of a freely falling curtain of a coating liquid which falls from the lip of the hopper and, under gravity, encounters the item moving through the curtain so as to form a coat (or a coating). This technique has been widely used in the field of the preparation of multilayer photosensitive silver supports (see for example U.S. Pat. Nos. 3,508,947, 3,508,947 or EP537086).

It is known that the quality of the coating depends on the quality of the freely falling curtain. It is preferable for the curtain to have a stable laminar flow from the place where it forms to the line of encounter with the moving support. If this is not the case, the surface tension will lead the curtain to contract toward the interior and to interrupt the laminar flow. In order to prevent this problem, it is known practice to use edge guides to seize the freely falling curtain at its edges and to prevent it from contracting toward the interior owing to the surface tension. Examples of such systems are described in U.S. Pat. Nos. 4,933,215, 4,479,987, 4,974,533, 3,632,374, 4,479,987, EP537086 and 4,830,887.

Another subject of the invention relates to a mammary prosthesis comprising a polyurethane pouch containing the silicone gel G according to the invention and as defined above.

The final subject of the invention relates to a cushion or mattress for preventing pressure sores, comprising the silicone gel G according to the invention and as defined above.

The nonlimiting examples which follow show various possibilities of formulation of the compositions according to the invention and also the characteristics and the properties of the silicone gels obtained by crosslinking said compositions.

EXAMPLES

1) Measurement of the Tack:

The test is carried out according to the standard ASTM D2979 with a PROBE TACK device (PT-1000). A cylindrical punch with a flat face is brought into contact with the gel of the composite to be tested (surface area of contact with the gel=0.2 cm$^2$). The composite consists of a (paper-supported) flexible polyurethane film coated with 200 g/m$^2$ of the silicone composition which is a precursor of the gel. The punch is then kept in contact with the gel for a contact time of 1 second at a constant pressure of 100 gf/cm$^2$. Next, the punch is detached from the gel at a constant speed of 10 mm/s, and the detachment energy required to separate the gel from the rod is measured and expressed in mJ/cm$^2$.

2) Evaluation of the Adhesion ("Rub-Off") of the Silicone Gel to the Support Which is a Flexible Polyurethane Film and of the Quality of the Gel The adhesion of the silicone gel to the support which is a flexible polyurethane film or "Rub-Off") measurement consists of a qualitative evaluation of the resistance of the gel during scrubbing with the finger. The surface of the gel is rubbed with the finger and the number of (forward-and-back) passes of the finger is counted until a delamination appears. The gel will be considered to be more adhesive to the polyurethane film if the number of passes of the finger is higher before observing the delamination of the gel from its substrate. Above 30 "scrubbings" forward-and-back with the finger, it is considered that the adhesion to the polyurethane support is satisfactory.

The quality of the gel is evaluated by means of a penetrometer (PEN) according to the standard NF ISO 2137, using a Petrotest penetrometer, model PNR 12, with a total weight of the rod and cone fixed at 62.5 g. The cone penetrability of a silicone gel is determined at 25° C. by measuring the depth of penetration of the cone into the sample, said depth being obtained by releasing the cone assembly of the penetrometer and leaving the cone to act for 5 seconds. The results are expressed in tenths of a mm (mm/10).

3) Preparation of the Gel Precursor Silicone Compositions According to the Invention a) Starting Materials Used POS B1=α,ω-(dimethylvinylsiloxy) polydimethylsiloxane oil having a dynamic viscosity at 25° C. equal to 60 000 mPa·s.

POS B2=α,ω-(dimethylvinylsiloxy) polydimethylsiloxane oil having a dynamic viscosity at 25° C. equal to 1000 mPa·s.

POS CE=poly(dimethylsiloxy)-α, ω dimethylhydrosiloxy oil having a viscosity of approximately 8.5 mPa·s, containing on average 5.7% by weight of SiH unit, having a structure of the $M^H D_x M^H$ type with x between on average 7 and 15 and having a (number of SiH groups)/(total number of silicon atoms) ratio=0.154;

POS $XL^1$=poly(dimethylsiloxy) (methylhydrosiloxy) α, ω dimethylhydrosiloxy oil having an average viscosity of 22 mPa·s, containing 20.00% by weight of SiH groups (or 0.694% by weight of hydrogen atom originating from SiH functions) per polymer and having a structure of the $M^H D_x D_w^G M^H$ type with x between on average 18 and 20 and w on average between 15 and 17 and having a (number of SiH groups)/(total number of silicon atoms) ratio=0.478;

POS $XL^2$=poly(dimethylsiloxy) (methylhydrosiloxy) α, ω dimethylhydrosiloxy oil having an average viscosity of 40 mPa·s, containing 30.50% by weight of SiH groups (or 1.059% by weight of hydrogen atom originating from SiH functions) per polymer and having a structure of the $M^H D_x D_w^H M^H$ type with x between on average 17 and 19 and w on average between 36 and 38 and having a (number of SiH groups)/(total number of silicon atoms) ratio=0.655;

Hydrosilylation catalyst E (Cate E)=organometallic platinum complex (Karstedt Platinum) used as hydrosilylation reaction catalyst corresponding to 10% of platinum.

Inhibitor D=hydrosilylation reaction inhibitor=1-ethynyl-1-cyclohexanol (ECH)

b) Preparation of the Composites (=Support Coated with a Silicone Gel)

The silicone compositions tested are in the two-component form. The parts called Part A and Part B are then mixed in a 1:1 weight ratio. The composition before crosslinking is indicated in the table corresponding to the test. The silicone composition which is a precursor of a gel is then applied, at a content of 200 g/m², to a polyurethane support (paper-supported flexible film) using a coating scraper. After the coating, the crosslinking of the composite is carried out for 30 min at 120° C. in a ventilated oven so as to obtain a support coated with a gel. The results are reported in tables 1 and 2 below.

In these tables, the symbol "x" signifies that the measurement was not carried out since a "hard" silicone elastomer was obtained, that is to say different than a "silicone gel".

TABLE 1

Properties of the gels obtained from a composition comprising a POS $XL^1$ crosslinker containing 20.00% by weight of SiH groups per polymer.

| | Test No. | | | | | | |
|---|---|---|---|---|---|---|---|
| | C-1 | C-2 | C-3 | C-4 | C-5 | I-6 | I-7 |
| Parts by weight (per 100 parts of the composition) | | | | | | | |
| POS B1 | 93.04 | 92.54 | 90.26 | 89.56 | 88.08 | 87.38 | 84.55 |
| POS B2 | 4.45 | 4.45 | 4.47 | 4.47 | 4.45 | 4.45 | 4.45 |
| ECH | 0.0060 | 0.0060 | 0.0060 | 0.0060 | 0.0060 | 0.0060 | 0.0060 |
| POS CE | 2.00 | 2.00 | 5.00 | 4.95 | 7.00 | 8.00 | 10.74 |
| POS $XL^1$ | 0.50 | 1.00 | 0.25 | 1.00 | 0.45 | 0.15 | 0.25 |
| Pt Catalyst | 0.0055 | 0.0055 | 0.0055 | 0.0055 | 0.0055 | 0.0055 | 0.0055 |
| Calculations ratios of the silicone compositions which are precursors of a gel | | | | | | | |
| RHAlk | 2.3 | 3.5 | 3.5 | 5.3 | 5.3 | 5.2 | 7.3 |
| $RH^{CE}V$ | 1.15 | 1.16 | 2.95 | 2.94 | 4.22 | 4.86 | 6.71 |
| $RH^{CE}$ | 50.12 | 33.44 | 83.40 | 55.42 | 79.62 | 93.05 | 91.53 |
| Properties of the gels obtained after crosslinking | | | | | | | |
| Physycal state = gel | No | No | Yes | No | No | Yes | Yes |
| Penetrometry (mm/10) | x | x | 124 | 23 | 63 | 270 | 189 |
| Tack (mJ/cm²) | x | x | 11 | <5 | 11 | 25 | 25 |
| Rub off number of passages | x | x | >50 | x | >50 | 25 | 25 |
| Gel adhesive to polyurethane support and having a good track (>14 mJ/cm²) | No | No | No | No | No | Yes | Yes |

TABLE 2

Properties of the gels obtained from a composition comprising a POS XL$^2$ crosslinker containing 30.5% by weight of SiH groups per polymer.

| | \multicolumn{12}{c}{Test No.} |
|---|---|---|---|---|---|---|---|---|---|---|---|---|
| | C-8 | C-9 | C-10 | C-11 | C-12 | C-13 | C-14 | C-15 | I-16 | C-17 | I-18 | I-19 |
| | \multicolumn{12}{c}{Parts by weight (per 100 parts of the composition)} |
| POS B1 | 94.79 | 93.29 | 91.14 | 91.54 | 90.69 | 88.29 | 87.54 | 85.29 | 77.28 | 79.54 | 74.78 | 70.44 |
| POS B2 | 4.449 | 4.451 | 4.449 | 4.450 | 4.451 | 4.450 | 4.450 | 40450 | 4.451 | 4.450 | 4.451 | 4.438 |
| ECH | 0.006 | 0.006 | 0.006 | 0.006 | 0.006 | 0.006 | 0.006 | 0.006 | 0.006 | 0.006 | 0.006 | 0.006 |
| POS CE | 0.50 | 2.00 | 4.25 | 3.75 | 4.75 | 7.00 | 7.50 | 10.00 | 18.01 | 15.00 | 20.51 | 24.86 |
| POS XL$^2$ | 0.25 | 0.25 | 0.15 | 0.25 | 0.10 | 0.25 | 0.50 | 0.25 | 0.25 | 1.00 | 0.25 | 0.25 |
| Pt Catalyst | 0.0055 | 0.0055 | 0.0055 | 0.0055 | 0.0055 | 0.0055 | 0.0055 | 0.0055 | 0.0055 | 0.0055 | 0.0055 | 0.0055 |
| | \multicolumn{12}{c}{Calculations ratios of the silicone compositions which are precursors of a gel} |
| RHAlk | 1.1 | 1.9 | 2.9 | 3.0 | 3.1 | 5.0 | 6.2 | 7.0 | 13.0 | 13.4 | 15.1 | 19.0 |
| RH$^{CE}$V | 0.28 | 1.14 | 2.46 | 2.16 | 2.76 | 4.17 | 4.50 | 6.14 | 12.05 | 9.79 | 14.11 | 18.02 |
| RH$^{CE}$ | 26.47 | 59.02 | 83.61 | 72.97 | 89.53 | 83.44 | 72.97 | 87.80 | 92.84 | 72.97 | 93.65 | 94.74 |
| | \multicolumn{12}{c}{Properties of the gels obtained after crosslinking} |
| Physical state = gel | No | No | Yes | No | Yes | No | No | No | Yes | No | Yes | Yes |
| Penetrometry (mm/10) | x | x | 139 | 64 | 224 | x | x | x | 95 | x | 118 | 125 |
| Tack (mJ/cm$^2$) | x | x | 13 | 11 | 13 | x | x | x | 14 | x | 15 | 15 |
| Rub off number of passages | x | x | x | >50 | >50 | x | x | x | >50 | x | >50 | >50 |
| Gel adhesive to polyurethane support and having a good track (>14 mJ/cm$^2$) | No | No | No | No | No | No | No | No | Yes | No | Yes | Yes |

The invention claimed is:

1. A silicone composition A which is a precursor of a silicone gel G and which is crosslinkable by hydrosilylation, the silicone composition A comprising:
1) at least one organopolysiloxane B comprising:
   (i) at least two siloxyl units of formula (B1):

$$(Y)_a(Z)_b SiO_{(4-(a+b))/2} \quad (B1)$$

in which:
   Y represents a monovalent radical containing from 2 to 6 carbon atoms, having at least one alkenyl group,
   Z represents a monovalent radical containing from 1 to 20 carbon atoms and not comprising an alkenyl group;
   a and b represent integers, a being 1, 2 or 3, b being 0, 1 or 2 and (a+b) being 1, 2 or 3;
   (ii) and optionally comprising other siloxyl units of formula (B2):

$$(Z)_c SiO_{(4-c)/2} \quad (B2)$$

in which:
   Z has the same meaning as above, and
   c represents an integer which is 0, 1, 2 or 3,
2) at least one organopolysiloxane CE comprising:
   two siloxyl end units, which are identical or different, of formula (CE-1):

$$(H)_p(R^1)_q SiO_{1/2} \quad (CE-1)$$

in which:
   the symbol R$^1$ corresponds to a C$_1$ to C$_8$ alkyl group or to a C$_6$ to C$_{10}$ aryl group;
   and the symbol H represents a hydrogen atom, with p=0 or 1, q=2 or 3 and (p+q)=3;
   at least one siloxyl unit of formula (CE-2):

$$(H)_n(R^2)_m SiO_{2/2} \quad (CE-2)$$

in which the radical R$^2$ corresponds to a C$_1$ to C$_8$ alkyl group or a C$_6$ to C$_{10}$ aryl group, the symbol H represents a hydrogen atom and with n=0 or 1, m=1 or 2 and (n+m)=2, and
   with the condition according to which the organopolysiloxane CE contains two hydrogen atoms each one bonded to a different silicon atom per polymer;
3) at least one organopolysiloxane XL comprising:
   at least three siloxy units of formula (XL-1):

$$(H)(L)_e SiO_{(3-e)/2} \quad (XL-1)$$

in which the symbol H represents a hydrogen atom, the symbol L represents an alkyl having from 1 to 8 carbon atoms inclusive or a C$_6$ to C$_{10}$ aryl, and the symbol e is equal to 0, 1 or 2; and
   optionally other siloxy units of formula (XL-2):

$$(L)_g SiO_{(4-g)/2} \quad (XL-2)$$

in which the symbol L represents an alkyl having from 1 to 8 carbon atoms inclusive or a C$_6$ to C$_{10}$ aryl and the symbol g is equal to 0, 1, 2 or 3, and
   with the condition according to which the organopolysiloxane XL contains from 15.1% to 40.0% by weight of Si—H function per polymer,
4) an effective amount of at least one hydrosilylation catalyst E,
5) at least one hydrosilylation reaction inhibitor D,
6) optionally at least one additive K, and the weight amounts of the organopolysiloxanes B, CE and XL are chosen so as to satisfy the following three conditions:
a) the molar ratio $RHAlk = tH/tAlk \geq 3.0$;
b) the molar ratio $RH^{CE}V = nH^{CE}/tAlk \geq 4.50$, and
c) the mol % $RH^{CE} = (nH^{CE}/tH) \times 100$ is greater than or equal to 90 mol %, with:

tH=number of moles of hydrogen atom directly bonded to a silicon atom of the organopolysiloxanes CE and XL, tAlk=number of moles of alkenyl directly bonded to a silicon atom of the organopolysiloxane B; and $nH^{CE}$=number of moles of hydrogen atom directly bonded to a silicon atom of the organopolysiloxane CE.

2. The silicone composition A as claimed in claim 1, wherein:
the organopolysiloxane B has a dynamic viscosity at 25° C. of from 100 mPa·s to-120,000 mPa·s,
the organopolysiloxane CE has a dynamic viscosity at 25° C. of from 1 mPa·s to 500 mPa·s, and
the organopolysiloxane XL has a dynamic viscosity at 25° C. of from 5 mPa·s to 2,000 mPa·s.

3. The silicone composition A as claimed in claim 2, wherein the nature and the weight amounts of the organopolysiloxanes B, CE and XL are chosen such that the dynamic viscosity at 25° C. of the silicone composition X is from 200 mPa·s to 100,000 mPa·s.

4. The silicone composition A as claimed in claim 1, wherein the composition comprises at least two organopolysiloxanes B comprising, per molecule, at least two $C_2$ to $C_6$ alkenyl radicals each bonded to a silicon atom, the first having a dynamic viscosity at 25° C. of from 50,000 mPa·s to 120,000 mPa·s, and the second having a dynamic viscosity at 25° C. of from 500 mPa·s to 20,000 mPa·s.

5. A silicone gel G obtained by crosslinking of the composition A as defined in claim 1, optionally by heating at a temperature of from 70° C. to 200° C. and/or under the action of infrared radiation.

6. The silicone gel G as defined in claim 5, wherein the gel is in a medical device selected from the group consisting of a mammary prosthesis, an adhesive dressing that adheres to the skin or a device for holding in place medical accessories used in contact with the skin, of sensor, probe, catheter and needle type.

7. An item which adheres to the skin, the item comprising a substrate S which is a plastic film, optionally a polyester or polyurethane film, continuously or discontinuously coated onto at least one of the two faces with a silicone gel G as claimed in claim 5.

8. The item as claimed in claim 7, wherein the substrate S is a perforated flexible polyurethane film or a continuous flexible polyurethane film.

9. A dressing or patch for medical or paramedical use, the dressing or patch that comprising an item that adheres to the skin as described in claim 7.

10. A mammary prosthesis comprising a polyurethane pouch comprising the silicone gel G as defined in claim 5.

11. A cushion or mattress for minimizing pressure sores, the cushion or mattress comprising the silicone gel G as defined in claim 5.

12. The silicone composition A as claimed in claim 1, wherein the polyorganosiloxane CE contains, per polymer two siloxyl units of formula (CE-1) in which p=1 and at least one siloxyl unit of formula (CE-2) in which n=0.

13. The silicone composition A as claimed in claim 1, wherein organopolysiloxane XL has from 18% to 35.0% by weight of Si—H function per polymer.

14. The silicone composition A as claimed in claim 1, wherein the molar ratio is $3.0 \leq RHAlk \leq 24$.

15. The silicone composition A as claimed in claim 14, wherein the molar ratio is $4.5 \leq RHAlk \leq 20$.

16. The silicone composition A as claimed in claim 1, wherein the molar ratio is $4.50 \leq RH^{CE}V \leq 20$.

17. The silicone composition A as claimed in claim 1, wherein the mol % $RH^{CE} = (nH^{CE}+H) \times 100$ is from 90 mol % to 95 mol %.

18. The silicone composition A as claimed in claim 1, wherein CE has a dynamic viscosity at 25° C. of from 5 to 200 mPa·s.

19. The silicone composition A as claimed in claim 1, wherein XL has a dynamic viscosity at 25° C. from 5 to 500 mPa·s.

20. The silicone composition A claim 2, wherein the dynamic viscosity of silicone composition X is from 200 mPa·s to 80,000 mPa·s.

* * * * *